United States Patent [19]

Malis et al.

[11] Patent Number: 5,443,197
[45] Date of Patent: Aug. 22, 1995

[54] LOCKING MECHANISM FOR A SKIN STAPLER CARTRIDGE

[75] Inventors: Michael J. Malis, Trumbull; Gilbert J. Neagle, West Haven, both of Conn.

[73] Assignee: United States Surgical Corporation, Norwalk, Conn.

[21] Appl. No.: 78,942

[22] Filed: Jun. 16, 1993

[51] Int. Cl.[6] .......................................... A61B 17/068
[52] U.S. Cl. .................................. 227/176; 227/19
[58] Field of Search ............... 227/19, 175, 176, 177, 227/178, 179, 180, 181, 182

[56] References Cited

U.S. PATENT DOCUMENTS

| | | |
|---|---|---|
| Re. 28,932 | 5/1975 | Noiles et al. |
| 3,618,842 | 3/1970 | Bryan. |
| 3,638,847 | 2/1972 | Noiles et al. |
| 3,643,851 | 2/1972 | Green et al. |
| 3,650,453 | 3/1972 | Smith, Jr. |
| 3,662,939 | 5/1972 | Bryan. |
| 3,717,294 | 2/1973 | Green. |
| 3,740,994 | 6/1973 | DeCarlo, Jr. |
| 3,819,100 | 6/1974 | Noiles et al. |
| 3,949,924 | 4/1976 | Green. |
| 3,955,581 | 5/1976 | Spasiano et al. |
| 4,204,623 | 5/1980 | Green. |
| 4,349,028 | 9/1982 | Green. |
| 5,114,065 | 5/1992 | Storace ............... 227/19 X |
| 5,251,801 | 10/1993 | Ruckdeschel et al. ......... 227/19 X |
| 5,258,010 | 11/1993 | Green et al. |

OTHER PUBLICATIONS

"Auto Suture® LDS-2 Surgical Stapling Instrument" Information Booklet United States Surgical Corporation (1977).

Primary Examiner—Rinaldi I. Rada

[57] ABSTRACT

A locking mechanism for a surgical stapler includes a movable projection and a notch for receiving the movable projection. The notch is at least partially defined by an abutment surface for contacting the projection to inhibit movement relative movement between the projection and reception means in a direction orthogonal to the direction of movement of the projection.

17 Claims, 5 Drawing Sheets

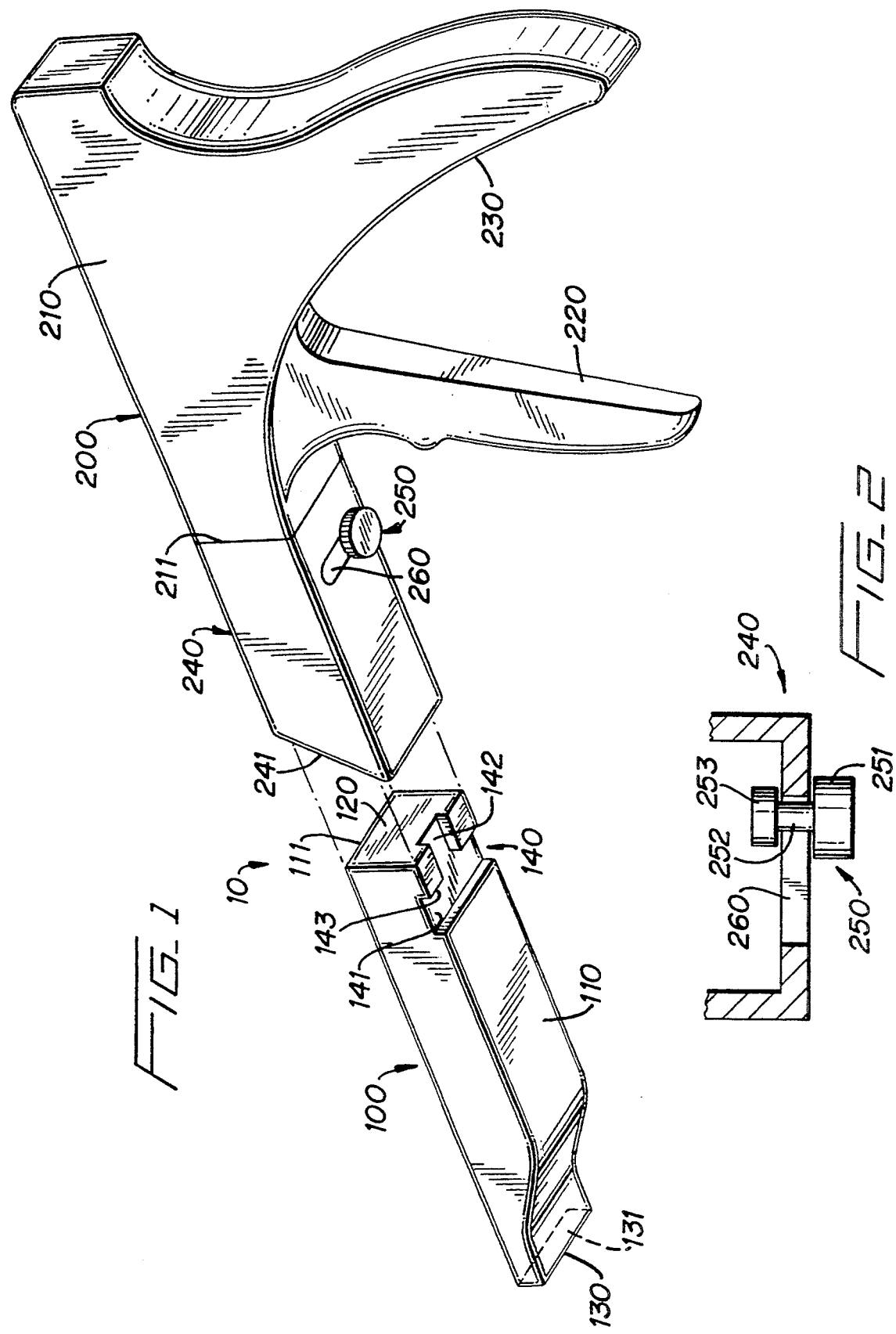

LOCKING MECHANISM FOR A SKIN STAPLER CARTRIDGE

BACKGROUND OF THE INVENTION

1. Field of the Invention

The present invention relates to a surgical skin stapler having a removable and replaceable cartridge. More particularly, the present invention relates to a locking mechanism for securing a cartridge inserted into the stapler.

2. Background of the Art

Surgical apparatus for stapling together disunited segments of external skin or internal fascia of a patient are known in the art. Such staplers are generally hand held and apply metal or polymeric staples.

A manually powered surgical stapling instrument is disclosed in U.S. Pat. No. 4,204,623 to Green, herein incorporated by reference.

A pneumatically powered surgical stapler is disclosed in U.S. Pat. No. 3,643,851, here incorporated by reference.

Other references which disclose surgical staplers and/or related components, such as cartridges, include U.S. Pat. Nos. 3,662,939; Re. 28,932; 3,618,842; 3,638,847; 3,650,453; 3,717,294; 3,819,100; 3,949,924; and 3,955,581, all of which are herein incorporated by reference.

Surgical stapling apparatus generally comprise a main body portion optionally having a nose portion rotatably mounted therein and adapted to receive and mount a staple carrying cartridge. The cartridge generally includes pusher means for advancing the staples and, optionally, means for forming the staples as they are ejected. Means are provided in the stapler body for driving the pusher element of the staple carrying cartridge to advance, eject and optionally form the staples. Some staplers include a thrust bar slidably mounted for reciprocating movement. The thrust bar is advanced with sufficient speed and force to drive the staple into the skin or fascia. The cartridge of prior known staplers snap-fit into the stapler nose portion, and are removable with a tug.

In one type of known apparatus referred to as the Auto Suture LDS-2* stapler marketed by the assignee of this application, a cartridge includes a projection with side pins which fit into corresponding slots in the apparatus body when the cartridge and apparatus body are assembled. A slide lock is then advanced over the slots to prevent the side pins from moving out of the slots, thereby locking the cartridge in place.

Although these cartridges are securely held in the instrument nose, the present invention provides an alternative mode of securement of the cartridge which utilizes a release mechanism.

SUMMARY OF THE INVENTION

A surgical stapler is provided herein which comprises a cartridge for holding a plurality of surgical staples; a stapler body for receiving the cartridge and having means for firing the staples from the cartridge in response to a user applied actuation force; and locking means movable between a locked configuration for locking the cartridge in the stapler body and an unlocked configuration for permitting engagement and disengagement of the cartridge from the stapler body. The locking means includes first means having a projection which is movable with respect to the stapler body and which is engageable with reception means for receiving the projection. The reception means has at least one abutment surface for contacting the projection to inhibit relative movement between the projection and the reception means in a direction orthogonal to the direction of movement of the projection with respect to the stapler body.

In one embodiment the stapler body includes an elongated laterally oriented slot having first and second ends and the first means comprises a locking member slidably movable within the slot between the first and second ends in response to user applied pressure. The locking member comprises a knob portion for receiving user applied pressure, the knob portion being connected to one end of a shaft portion located within the slot, and the projection being connected to the other end of the shaft portion. The reception means comprises a notch in the exterior surface of the cartridge, the notch having an access portion for permitting slidable entry therein of the projection during insertion and removal of the cartridge from the stapler body when the projection is positioned at said first end of the slot. The notch also has a locking portion at least partially defined by the abutment surface for receiving the projection when the projection is moved to the second end of said slot, the abutment surface being located proximal to the projection when the locking means is in the locked configuration. Preferably, the knob portion and the projection both have diameters greater than the width of the slot.

In another embodiment the first means comprises a bar mounted to the stapler body and pivotally movable between the locked configuration and unlocked configuration, a push button connected to one end of the bar for receiving user applied pressure to move the first means to the unlocked configuration. The projection is connected to the other end of the bar. The bar is resiliently biased to the locked configuration. The reception means comprises a notch in the exterior surface of the cartridge for receiving the projection, the notch being at least partially defined by the abutment surface, and the abutment surface being located proximal to the projection when the first means is in the locked configuration.

In yet another embodiment the stapler body includes a chamber, the projection being movable between a first position completely within the chamber wherein the locking means is in the unlocked configuration, and a second position in which at least part of the projection is located outside said chamber wherein the locking means is in the locked configuration. The projection is resiliently biased to the second position. The reception means comprises a notch in the exterior surface of the cartridge for receiving the projection, the notch being at least partially defined by the abutment surface. The abutment surface is located proximal to the projection when the projection is in the second position.

The present invention advantageously provides means for securely locking the cartridge within the stapler thereby preventing the unintended dislodging of the cartridge from the stapler.

BRIEF DESCRIPTION OF THE DRAWINGS

FIG. 1 is an exploded perspective view of the apparatus.

FIG. 2 is a partly sectional view of the locking mechanism of the present invention.

DETAILED DESCRIPTION OF PREFERRED EMBODIMENTS

Figure 3:
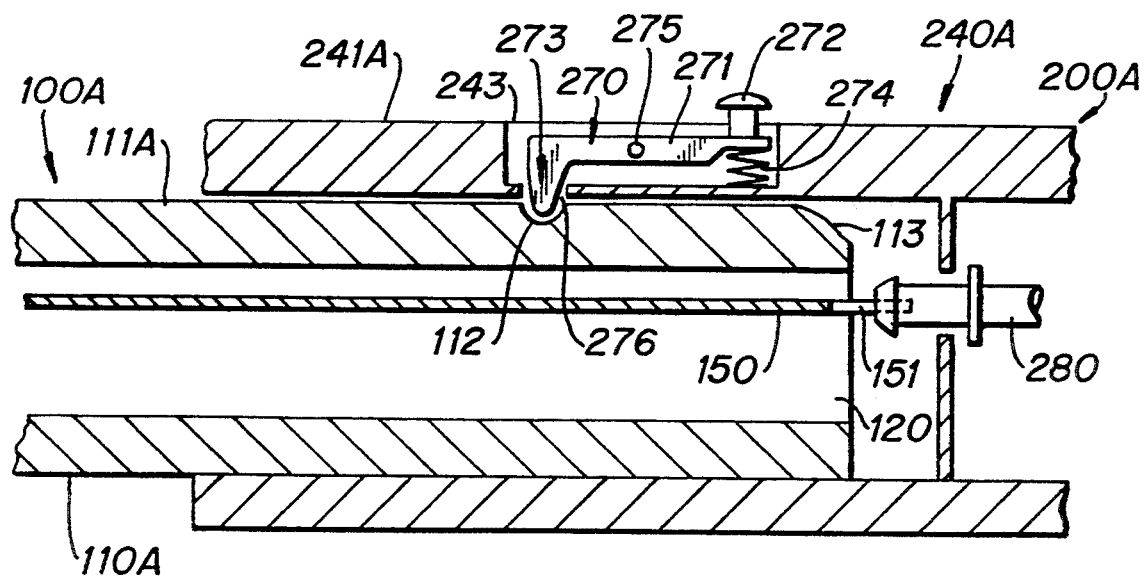
FIG. 3 is a sectional view of an alternative embodiment of the locking mechanism of the present invention.

Generally the skin stapler of the present invention includes a hand held stapler body and a replaceable elongated cartridge which is insertable in the nose portion of the stapler body. The skin stapler sequentially applies surgical staples to skin or fascia. The staples are applied one at a time, one staple being applied with each firing sequence. The tissue is approached from only one side, i.e. the tissue is not placed between instrument jaws. The longitudinal axis of the cartridge is aligned with the longitudinal axis of the instrument and the cartridge is inserted longitudinally into the distal opening of the stapler body. The staples are ejected from the distal end of the cartridge. The stapler body optionally possesses a longitudinally extending spring powered thrust bar which engages a staple pusher bar in the cartridge as discussed in U.S. Pat. No. 5,258,010, herein incorporated by reference. When the trigger is pulled the thrust bar is initially pulled back (proximally) against the biasing force of the spring, thereby drawing the staple pusher bar back to permit alignment of a staple in the drive path of the cartridge. The thrust bar then snaps forward in a powerful stroke to drive the staple pusher distally, thereby firing a staple out of the distal end of the cartridge and into body tissue. In other instruments the cartridge can optionally have an anvil at its distal end to form the staples as they are ejected.

The staples can be metal, which are usually formed by an anvil during application, or bioabsorbable polymeric staples which, unlike metal staples, do not need to be removed. Bioabsorbable staples can be fabricated, for example, from one or more of the bioabsorbable polymers such as polylactide, polyglycolide, polycaprolactone, polydioxanone, and trimethylene carbonate as individual homopolymers, polymer blends, or copolymers.

Referring to FIGS. 1 and 2, a skin stapler 10 is shown wherein staple holding cartridge 100 is removably insertable into the stapler body 200. Cartridge 100 includes a body having a proximal opening 120 for permitting contact between a thrust bar 280 of the stapler body (see FIG. 3), or other drive means, with the cartridge staple pusher 150 (see FIG. 3) mechanism. Nose portion 130 is a tapered portion having a distal opening 131 through which staples are ejected and optionally formed. Underside 110 includes one of the features of the cartridge lock mechanism, i.e., reception means for a locking projection. The reception means comprises a generally L-shaped notch 140 having a locking side portion 141 and a longitudinally oriented access portion 142. The locking side portion 141 is proximally bounded by abutment wall 143.

While the locking mechanism is shown as being positioned on the underside 110 of the nose 130, it should be understood that it may optionally be positioned on a top wall (111) or side walls. Abutment wall 143 at least partially defines locking side portion 141 and inhibits relative movement between projection 253 (discussed below) and the locking side portion in a longitudinal direction, which is orthogonal to the lateral or side to side movement of the projection.

The stapler body 200 of the apparatus includes a longitudinal upper body portion 210 for housing a drive mechanism, a handle 230, and a trigger 220. The stapler body 200 further includes a nose portion 240 having a distal opening 241 for receiving the proximal end of the cartridge 100, as illustrated. Optionally, nose portion 240 can be rotatable around joint 211 with respect to upper body portion 210, as seen for example in U.S. Pat. No. 4,204,623.

The nose portion 240 includes another feature of the cartridge lock of the present invention, the movable locking member 250. Locking member 250 is slidably mounted within lateral slot 260 in the nose portion 240 and is movable in response to force applied thereto by a user. Locking member 250 includes a knob 251 which is contacted by the finger of the user for moving the locking member 250 from side to side. A relatively narrow shaft 252 connects the knob 251 to an internal projection 253. Since shaft 252 is disposed through slot 260 and both the knob 251 and projection 253 have diameters greater than the width of slot 260, member 250 is slidable within slot 260 but not removable therefrom under normal conditions.

In operation, the locking member 250 is initially positioned at one side of the slot so that it is aligned with access portion 142 of notch 140. This portion permits cartridge 100 to be inserted into nose portion 240. When the cartridge is fully inserted, internal projection 253 will be positioned at the distal end of access portion 142 and laterally aligned with locking portion 141.

Also, once the cartridge is fully inserted into stapler body 200, the user slides the locking member 250 to the other side of the slot 260, thereby positioning internal projection 253 in locking portion 141 of notch 140. Once the internal projection is positioned therein, distal movement of the cartridge 100 with respect to stapler body 200 is prevented by the abutment of wall 143 against internal projection 253. Thus, the cartridge 100 is securely locked and cannot be removed except by deactivation of the lock, i.e., the user must laterally slide member 250 back to the initial position in order to remove cartridge 100 from the stapler body 200.

Referring to FIG. 3, a stapler apparatus with an alternative embodiment of the cartridge lock is illustrated wherein the cartridge 100A is inserted into nose portion 240A of the stapler body 200A. Staple pusher 150 engages the distal end of a thrust bar 280 upon insertion of the cartridge.

The second embodiment 270 of the cartridge lock includes a rocker arm 271 which is pivotally mounted by pin 275 in a slot 243 in wall 241A of the nose portion 240A. Wall 241A can be an upper wall, lower wall, or side wall. For purposes of exemplification, wall 241A is depicted as an upper wall although the placement of the lock on top, bottom, or side is not critical.

Rocker arm 271 includes a button 272 on its proximal end which projects above the upper surface of upper wall 241. At its distal end, rocker arm 271 has a downward pointing projection 273 which extends through aperture 276 and below the lower surface of upper wall 241A. Spring 274 biases the proximal end of the rocker arm upward and the distal end downward.

The cartridge 100A possesses an upper wall 111A having a notch 112 for receiving projection 273 of the rocker arm. Sloped proximal edge 113 permits entry of the cartridge 100 past projection 273 in the nose portion 240.

In use, the cartridge 100A is inserted into the nose portion 240 until notch 112 reaches projection 273 whereupon the two engage, optimally with an audible click. The cartridge is then securely locked in place. The instrument may then be used to implant staples in body tissue until the cartridge is empty of staples. To remove the cartridge the user presses down upon the button 272 against the biasing force of spring 274 whereupon the rocker arm 271 pivots and the projection 273 disengages from notch 112. The cartridge 100A may then be removed and replaced with a fresh cartridge.

Figure 4:
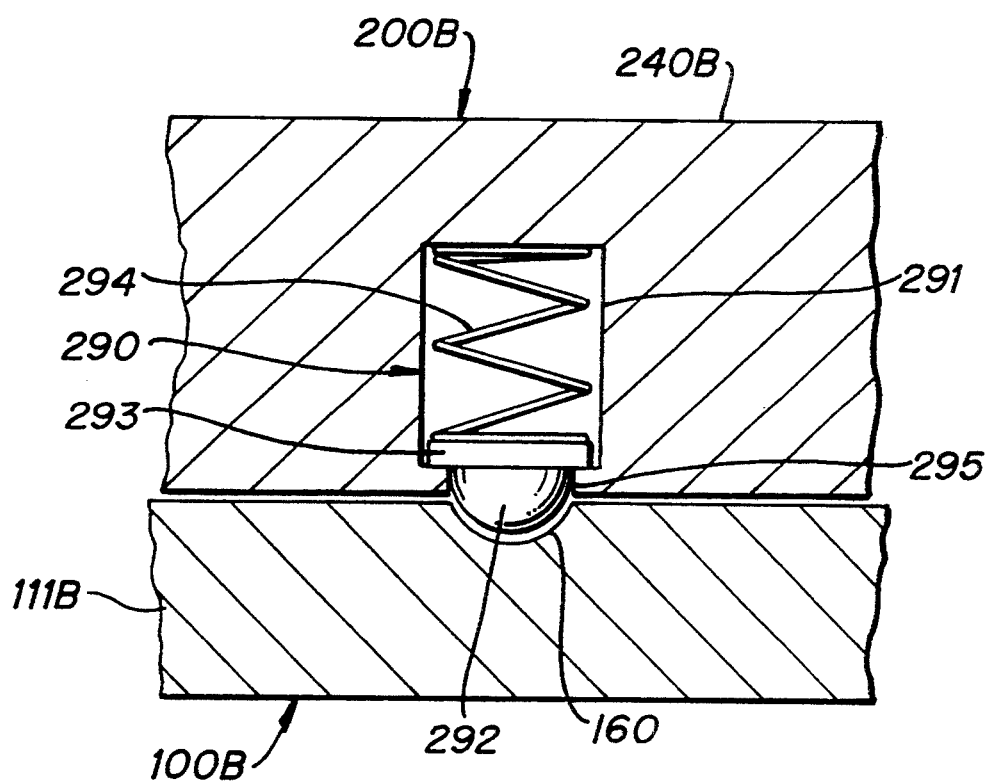
FIG. 4 is a partly sectional view of a third embodiment of the locking mechanism.

FIG. 4 illustrates a third embodiment of the present invention in which a cartridge lock 290 includes a spring biased projection 292 which engages a notch 160 in the cartridge. More particularly, projection 292 is mounted to plate 293 within chamber 291 in the nose portion 240B of the stapler body 200B. Plate 293 and projection 292 are biased by spring 294 such that projection 292 extends at least partially outside aperture 295. Cartridge 100B has a notch 160 in upper wall 111B for receiving projection 292.

In use, the cartridge is inserted into the nose 240B of the stapler body 200B until notch 160 is aligned with aperture 295. The projection 292 thereupon projects outside aperture 295 because of the biasing force of spring 294 and engages notch 160.

Projection 292 and notch 160 are shaped such that a strong longitudinal force on the cartridge will cause the sides and edges of the notch 160 to cam against the projection 292 to force it back into chamber 291 against the biasing force of the spring. Optimally, projection 292 is convex hemisphere and notch 160 is a concave hemisphere.

To remove the cartridge 100B, the user pulls it distally with sufficient force to overcome the locking force of spring 294. The force required to disengage the lock is greater than the forces normally occurring due to jostling or firing of the stapler.

Figure 5:
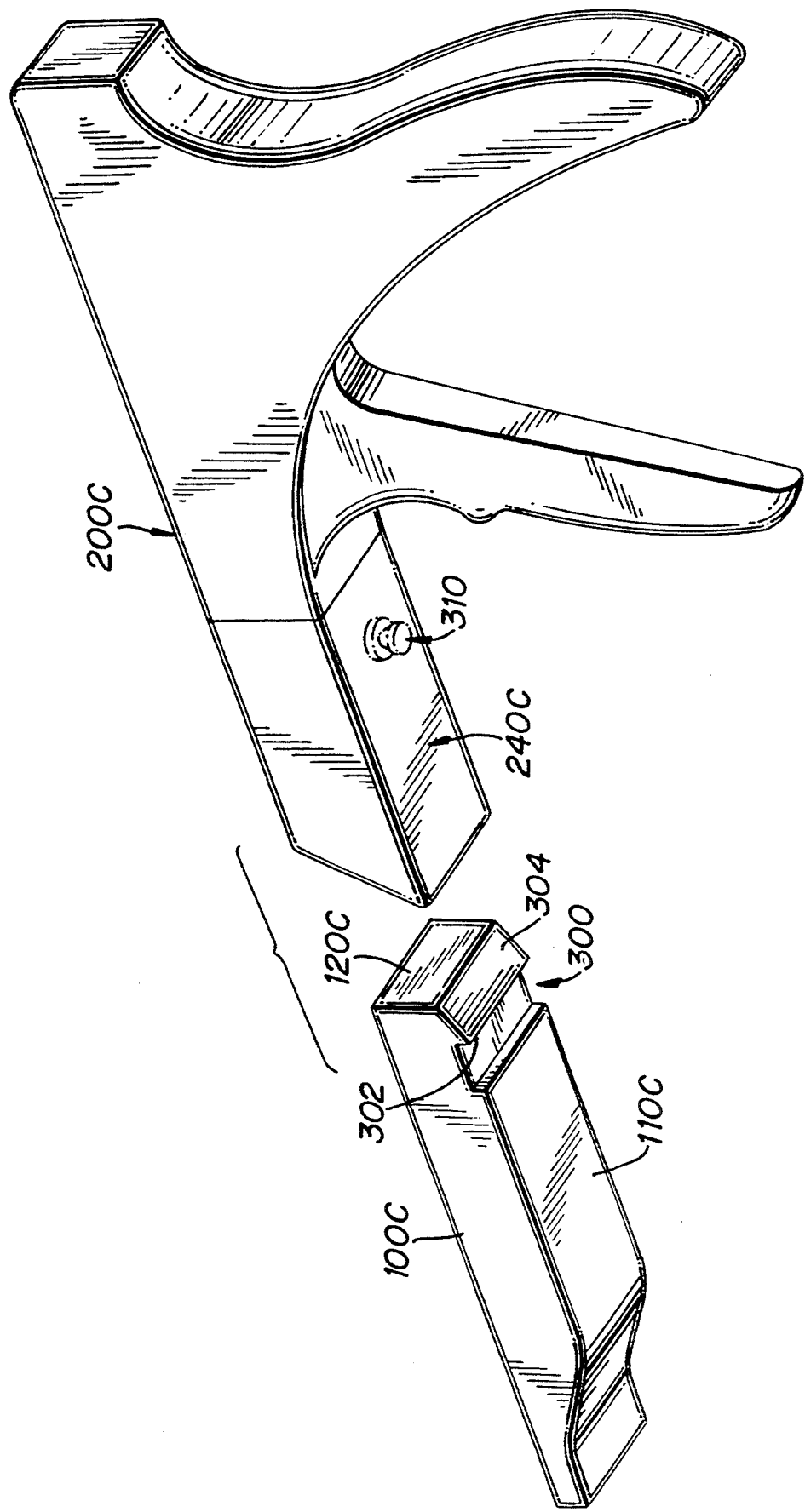
FIG. 5 is an exploded perspective view of a fourth embodiment of the invention.
Figure 6:
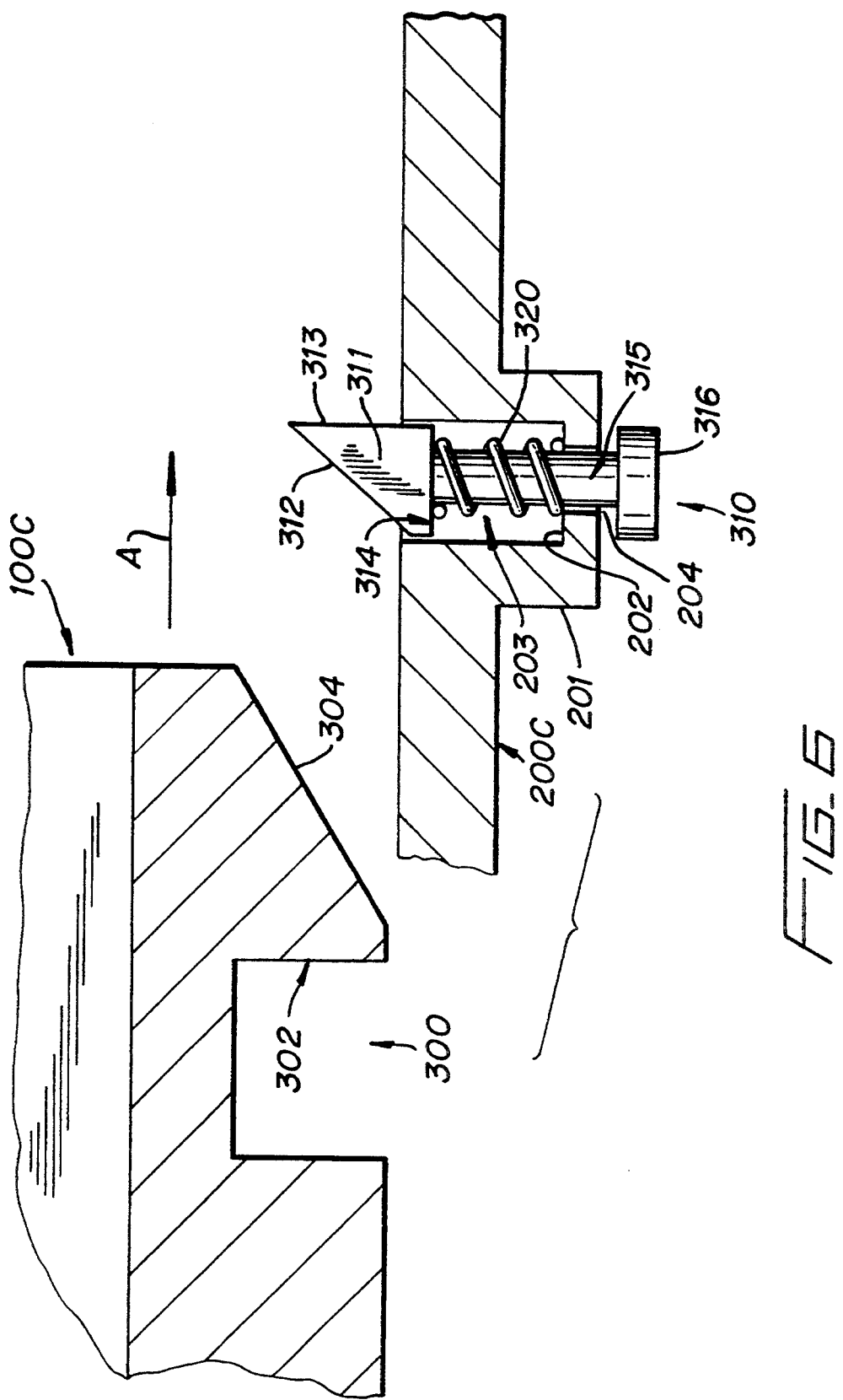
FIG. 6 is a partly sectional view of the fourth embodiment.

FIGS. 5 and 6 illustrate another embodiment of the present invention wherein the cartridge 100C includes a notch 300 extending laterally across the bottom surface 110C in the vicinity of the proximal end opening 120C. The notch 300 is proximally bordered by a vertical (as shown in FIG. 6) wall 302 which serves as an abutment surface. On the proximal side of wall 302 is an inclined wall 304 which serves as a camming surface.

The bottom of the nose portion 240C of the stapler body 200C includes a locking pin 310.

Referring to FIG. 6, locking pin 3 10 is seated in a chamber 203 formed by projecting wall 201, which extends downwardly from the nose portion 240C.

Pin 3 10 includes a notch-engaging portion 311 having an inclined distal surface 312, a substantially vertical (as shown in FIG. 6) wall 313, and a bottom surface 314. Pin 310 further includes shaft portion 315, which is disposed through aperture 204 in wall 201, and button 316, which is located outside the stapler body for contact by the user of the apparatus. Helical compression spring 320 is disposed around shaft 315 and biases the locking pin in the upward, i.e. locking, position. The ends of spring 320 abut bottom surface 314 of the notch-engaging portion 311, and surface 202 of chamber 203C.

In use, the cartridge is proximally inserted into distal opening 241C of the stapler body in the direction of arrow A. As camming surface 304 contacts surface 312 of the locking pin 310, portion 311 is moved downward against the biasing force of compression spring 320 until it fully enters chamber 203 to permit the cartridge 100C to pass over. When notch 300 becomes aligned with chamber 203 the locking pin 310 snaps upward and notch-engaging portion 311 engages the notch 300. The cartridge cannot thereafter be moved distally while the locking pin 310 is engaged with notch 300 due to the abutment of walls 313 and 302.

To remove the cartridge 100C from the stapler body 200C, the user manually grasps the button 316 and pulls down locking pin 310 to disengage notch-engaging portion 311 from notch 300, thereby permitting distal movement of the cartridge 100C.

The locking mechanism of the present invention can be fabricated from any material suitable for the functions discussed herein, such as polymer or metal. Moreover, the locking mechanism can be of any dimensions suitable for the use discussed herein.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A surgical stapler comprising:
   a) a cartridge for holding a plurality of surgical staples;
   b) a stapler body for receiving said cartridge and having drive means for firing said staples from said cartridge, said stapler body having a longitudinal axis along which said drive means is at least partially movable; and
   c) retaining means for retaining said cartridge in said stapler body, said retaining means moving between a locked configuration for locking said cartridge in said stapler body and an unlocked configuration for permitting engagement and disengagement of the cartridge from the stapler body, said retaining means including,
      i) a projection associated with the stapler body said projection being mounted to an elongated shaft, said shaft being oriented in a direction orthogonal to the longitudinal axis of the stapler body and mounted for sliding movement in a direction orthogonal to the longitudinal axis if the stapler body, and
      ii) reception means associated with the cartridge for receiving said projection, said reception means having at least one abutment surface for contacting said projection to inhibit relative movement between the projection and the reception means in the longitudinal direction.

2. The surgical stapler of claim 1 wherein said retaining means includes an elongated laterally oriented slot having first and second ends and said projection is slidably movable within said slot between said first and second ends in response to user applied pressure.

3. The surgical stapler of claim 2 wherein said retaining means comprises a knob portion for receiving user applied pressure, said knob portion being connected to one end of a shaft portion located within said slot, and said projection being connected to the other end of said shaft portion.

4. The surgical stapler of claim 3 wherein said reception means is located on an exterior surface of said cartridge.

5. The surgical stapler of claim 4 wherein said reception means comprises a notch, said notch having an access portion for permitting slidable entry therein of said projection during insertion and removal of said cartridge from said stapler body when said projection is positioned at said first end of said slot, and said notch having a locking portion at least partially defined by said abutment surface for receiving said projection when said projection is moved to said second end of said slot, said abutment surface being located proximal to said projection when said locking means is in said locked configuration.

6. The surgical stapler of claim 3 wherein said knob portion and said projection both have diameters greater than the width of said slot.

7. The surgical stapler of claim 1 wherein said stapler body includes a chamber, said projection being movable between a first position completely within said chamber wherein said retaining means is in said unlocked configuration, and a second position in which at least part of the projection is located outside said chamber wherein said retaining means is in said locked configuration.

8. The surgical stapler of claim 7 wherein said projection is resiliently biased to said second position.

9. The surgical stapler of claim 8 wherein said reception means comprises a notch in the exterior surface of said cartridge for receiving said projection, said notch being at least partially defined by said abutment surface, said abutment surface being located proximal to the projection when said projection is in said second position.

10. In a cartridge for use in an apparatus for applying a plurality of surgical fasteners, the apparatus having a projection movable with respect to the apparatus, said cartridge having a distal end and a proximal end which is longitudinally insertable and removable from said apparatus, an improvement which comprises:

a notch located on an outer surface of said cartridge for receiving the projection, said notch being at least partially defined by an abutment wall for contacting the projection to inhibit relative movement between the projection and said notch in a direction orthogonal to the direction of movement of the projection with respect to said apparatus, wherein the cartridge includes an inclined planar surface in the vicinity of the proximal end thereof and the projection includes an inclined planar surface on a distal side thereof for camming contact with said inclined planar surface of the cartridge.

11. In a surgical stapler body for receiving a staple holding cartridge having a notch formed in an outer wall and for firing staples therefrom, an improvement which comprises:

retaining means mounted to said surgical stapler body for retaining said cartridge in the stapler body, said retaining means including a movable projection for engaging a notch in the outer wall of said cartridge, and a release means responsive to actuation by a user for moving said movable projection.

12. The surgical stapler body of claim 11 wherein said retaining means includes a member mounted in a laterally oriented elongated slot in a wall of the stapler body and slidably movable therein from one end to the other of said elongated slot, said member having a shaft portion positioned within said elongated slot, a knob for receiving user applied force attached to one end of said shaft, said projection being attached to the other end of said shaft.

13. The surgical stapler body of claim 11 wherein said retaining means comprises a bar mounted to said stapler body and pivotally movable between a locked configuration and said release means comprising an unlocked configuration, a push button connected to one end of said bar and said projection being connected to the other end of said bar.

14. The surgical stapler body of claim 13 wherein said bar is resiliently biased to the locked configuration.

15. The surgical stapler body of claim 11 wherein said release means comprises a push button having a surface for direct contact by a user.

16. A surgical stapler comprising:
a housing having a longitudinal axis and means for receiving a cartridge containing fasteners; and mounting means for releasably mounting the cartridge to said housing, said mounting means being mounted for sliding movement in a direction transverse to said longitudinal axis, said mounting means including a shaft mounted to said housing for sliding movement and oriented in a direction transverse to said longitudinal axis of said housing, a projection mounted to said shaft and having a distal inclined surface and a proximal surface defining a plane which is perpendicular to said longitudinal axis of said housing, said projection being mounted for slidable movement between first and second positions, and means for biasing said projection to the first position.

17. A surgical stapler comprising:
a housing having a longitudinal axis and means for receiving a cartridge containing fasteners;
mounting means for releasably mounting the cartridge to said housing, said mounting means being mounted for sliding movement between a first position to retain the cartridge and a second position to release the cartridge; and
a user actuated release button for moving said mounting means from said first position to said second position.

* * * * *